(12) United States Patent
Yang et al.

(10) Patent No.: US 10,504,804 B2
(45) Date of Patent: Dec. 10, 2019

(54) LASER PROCESSING METHOD, SUBSTRATE DICING METHOD AND SUBSTRATE PROCESSING SYSTEM FOR PERFORMING THE SAME

(71) Applicant: SAMSUNG ELECTRONICS CO., LTD., Suwon-si, Gyeonggi-do (KR)

(72) Inventors: Jin-Yeol Yang, Cheonan-si (KR); Hyung-Su Son, Hwaseong-si (KR); Hae-Gu Lee, Asan-si (KR); Dong-Su Han, Hwaseong-si (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 16/039,622

(22) Filed: Jul. 19, 2018

(65) Prior Publication Data

US 2019/0131193 A1 May 2, 2019

(30) Foreign Application Priority Data

Oct. 27, 2017 (KR) .................. 10-2017-0141559

(51) Int. Cl.
*H01L 21/78* (2006.01)
*H01L 21/66* (2006.01)
(Continued)

(52) U.S. Cl.
CPC ............ *H01L 22/20* (2013.01); *B23K 26/359* (2015.10); *G01N 23/20* (2013.01); *H01L 21/78* (2013.01); *B23K 2101/40* (2018.08); *B23K 2103/56* (2018.08); *H01L 21/2633* (2013.01); *H01L 21/304* (2013.01); *H01L 21/6836* (2013.01); *H01L 2221/68327* (2013.01)

(58) Field of Classification Search
CPC ....................................... H01L 21/78
See application file for complete search history.

(56) References Cited

U.S. PATENT DOCUMENTS 6,072,854 A 6/2000 Kikuchi et al.
7,825,010 B2 * 11/2010 Clawson ........... H01L 21/67092
438/464

(Continued)

FOREIGN PATENT DOCUMENTS

JP 2016-094337 A 5/2016
JP 2016-216342 A 12/2016
(Continued)

OTHER PUBLICATIONS

Shul'Pina et al., "X-ray topographic study of defects in Si-based multilayer epitaxial power devices", Modern Electronic Materials, 2016, 2, 23-28.
(Continued)

*Primary Examiner* — Yu-Hsi D Sun
(74) *Attorney, Agent, or Firm* — Lee & Morse, P.C.

(57) ABSTRACT

A laser processing method includes irradiating a laser light into a substrate along a cutting line to form a laser-scribed layer within the substrate, irradiating an X-ray onto a first surface of the substrate along the cutting line, obtaining an image of a diffracted X-ray from the substrate, and determining whether or not the laser-scribed layer is formed along the cutting line, based on analysis of the obtained image of the diffracted X-ray.

20 Claims, 8 Drawing Sheets

(51) Int. Cl.
*B23K 26/359* (2014.01)
*G01N 23/20* (2018.01)
*B23K 103/00* (2006.01)
*H01L 21/263* (2006.01)
*H01L 21/683* (2006.01)
*B23K 101/40* (2006.01)
*H01L 21/304* (2006.01)

(56) References Cited

U.S. PATENT DOCUMENTS

| | | |
|---|---|---|
| 8,828,139 B2 | 9/2014 | Imai et al. |
| 8,895,363 B2 | 11/2014 | Buenning et al. |
| 9,422,639 B2 | 8/2016 | Sasaki |
| 2013/0323153 A1 | 12/2013 | Hoshi et al. |
| 2014/0132750 A1 | 5/2014 | Yoon et al. |
| 2017/0330745 A1 | 11/2017 | Nagashima et al. |

FOREIGN PATENT DOCUMENTS

| | | |
|---|---|---|
| KR | 10-2013-0071386 A | 6/2013 |
| KR | 10-1310292 B1 | 9/2013 |
| KR | 10-2014-0060946 A | 5/2014 |
| KR | 10-2016-0001425 A | 1/2016 |
| KR | 10-1715645 B1 | 3/2017 |
| WO | WO 2004/090522 A1 | 10/2004 |

OTHER PUBLICATIONS

E. Prieur et al., "X-Ray Topographic Contrast of Threading Dislocations in Silicon on Insulator Structures", Phys. Stat. Sol. (a) 158, 1996, pp. 19-34.

\* cited by examiner

LASER PROCESSING METHOD, SUBSTRATE DICING METHOD AND SUBSTRATE PROCESSING SYSTEM FOR PERFORMING THE SAME

CROSS-REFERENCE TO RELATED APPLICATION

Korean Patent Application No. 10-2017-0141559, filed on Oct. 27, 2017, in the Korean Intellectual Property Office, and entitled: "Laser Processing Method, Substrate Dicing Method and Substrate Processing Apparatus for Performing the Same," is incorporated by reference herein in its entirety.

BACKGROUND

1. Field

Example embodiments relate to a laser processing method, a substrate dicing method, and a substrate processing system for performing the same. More particularly, example embodiments relate to a laser processing method for dicing a substrate using a laser light, a substrate dicing method using the same, and a substrate processing system for performing the same.

2. Description of the Related Art

In order to cut an object, e.g., a semiconductor wafer or a glass substrate, using a laser light, the laser light having a wavelength to be absorbed by the object may be irradiated to form a modified region within the object along a cutting line, thereby dicing the object. The diced object may be inspected.

SUMMARY

According to example embodiments. Aa laser processing method includes irradiating a laser light into a substrate along a cutting line to form a laser-scribed layer within the substrate, irradiating an X-ray onto a first surface of the substrate along the cutting line, obtaining an image of a diffracted X-ray from the substrate, and determining whether or not the laser-scribed layer is formed along the cutting line, based on analysis of the obtained image of the diffracted X-ray.

According to example embodiments, in a substrate dicing method, a laser light is irradiated into a substrate along a cutting line to form a laser-scribed layer within the substrate. An X-ray is irradiated onto a first surface of the substrate along the cutting line. An image of a diffracted X-ray is obtained from the substrate. Whether or not the laser-scribed layer is formed along the cutting line is obtained from the X-ray diffraction image. The first surface of the substrate is grinded.

According to example embodiments, a substrate processing system includes a laser processing machine configured to irradiate a laser light into a substrate to form a laser-scribed layer within the substrate along a cutting line, and an X-ray topographic apparatus configured to detect the laser-scribed layer. The X-ray topographic apparatus includes a stage to support the substrate having the laser-scribed layer formed therein, an X-ray irradiator to irradiate an X-ray along the cutting line into the substrate, and an X-ray detector to obtain an image of a diffracted X-ray from the substrate.

BRIEF DESCRIPTION OF THE DRAWINGS

Features will become apparent to those of ordinary skill in the art by describing in detail exemplary embodiments with reference to the attached drawings, in which.

DETAILED DESCRIPTION

Hereinafter, example embodiments will be explained in detail with reference to the accompanying drawings.

Figure 1:
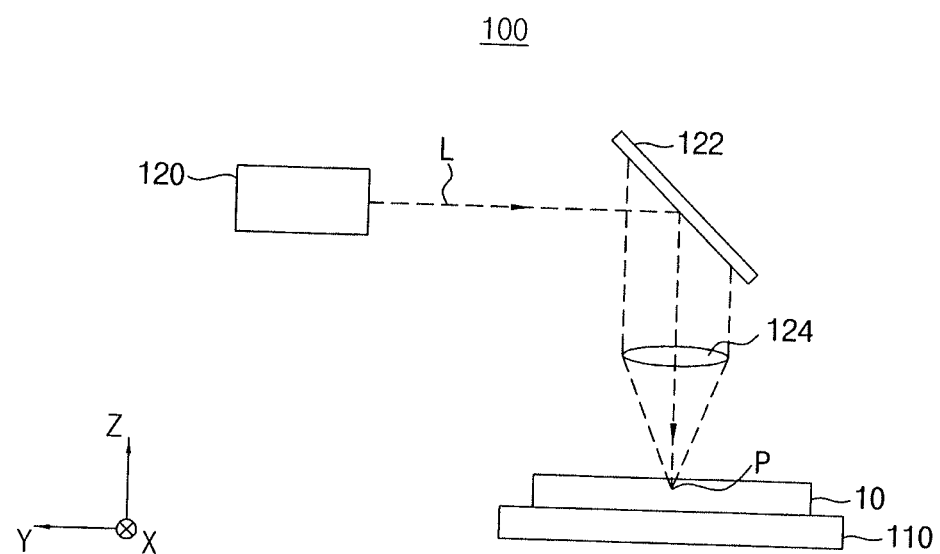
FIG. 1 illustrates a cross-sectional view of a laser processing machine of a substrate processing system in accordance with example embodiments.
Figure 2:
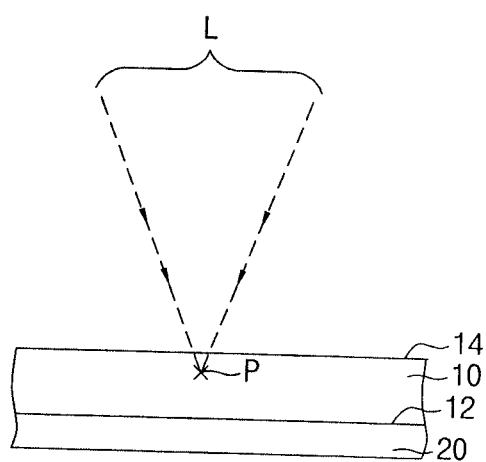
FIG. 2 illustrates a cross-sectional view of a wafer on which a laser light is irradiated by the laser processing machine in FIG. 1.
Figure 3:
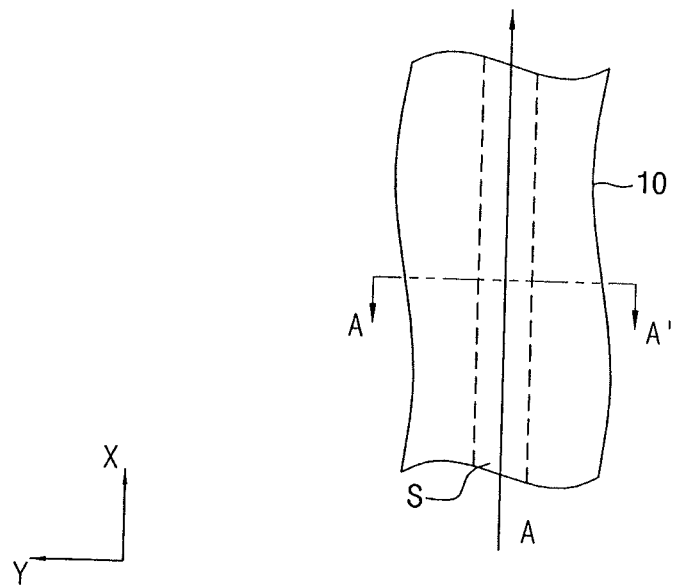
FIG. 3 illustrates a plan view of the wafer on which a laser processing process is performed by the laser processing machine in FIG. 1.
Figure 4:
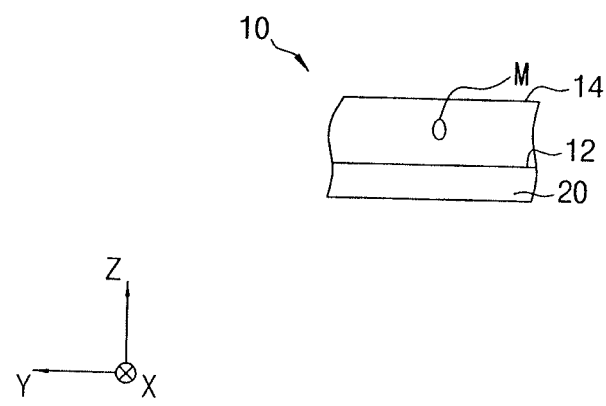
FIG. 4 illustrates a cross-sectional view taken along the line A-A' in FIG. 3.
Figure 5:
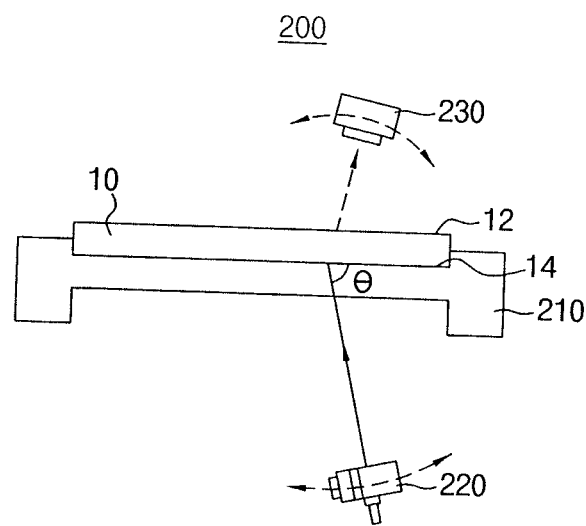
FIG. 5 illustrates a cross-sectional view illustrating an X-ray topographic apparatus of a substrate processing system in accordance with example embodiments.
Figure 6:
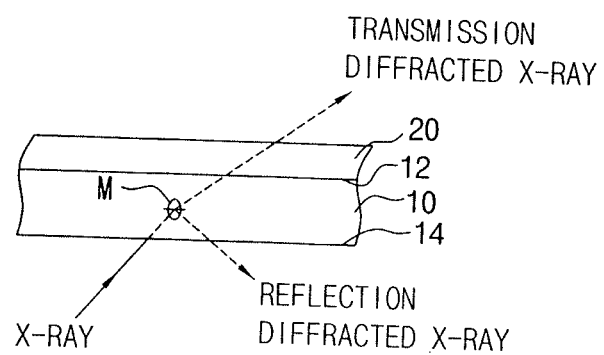
FIG. 6 illustrates a cross-sectional view of a wafer on which an X-ray is irradiated by the X-ray topographic apparatus in FIG. 5.

FIG. 1 is a cross-sectional view illustrating a laser processing machine of a substrate processing system in accordance with example embodiments. FIG. 2 is a cross-sectional view illustrating a wafer on which a laser light is irradiated by the laser processing machine in FIG. 1. FIG. 3 is a plan view illustrating the wafer on which a laser processing process is performed by the laser processing machine in FIG. 1. FIG. 4 is a cross-sectional view taken along the line A-A' in FIG. 3. FIG. 5 is a cross-sectional view illustrating an X-ray topographic apparatus of a substrate processing system in accordance with example embodiments. FIG. 6 is a cross-sectional view illustrating a wafer on which an X-ray is irradiated by the X-ray topographic apparatus in FIG. 5.

Referring to FIGS. 1 to 6, a substrate processing system in accordance with example embodiments may include a laser processing machine 100 configured to irradiate a laser light L into a substrate 10 to form a modified region M within the substrate 10, and an X-ray topographic apparatus 200 configured to detect the modified region M formed within the substrate 10. For example, the laser processing machine 100 and the X-ray topographic apparatus 200 may be in a single apparatus, e.g., incorporated together, or may be separate apparatuses within a system, e.g., so the substrate 10 may be transferred from the laser processing machine 100 to the X-ray topographic apparatus 200.

As illustrated in FIG. 1, in example embodiments, the laser processing machine 100 may irradiate the laser light L within the substrate 10 to apply a local high density energy into a focal position P in the substrate 10 to thereby form a stealth dicing layer as the modified region. In particular, the laser processing machine 100 may include a stage 110 to support the substrate 10 and to be movable along X, Y, Z axes, and a laser irradiator to irradiate the laser light L into the substrate 10.

For example, the laser irradiator may include a laser light source 120 which generates the laser light L, a reflection optic system 122 which reflects the laser light L emitted from the laser light source 120 to change the direction of the optic axis by 90°, and a condenser optic system 124 which converges the reflected laser light L toward the substrate 10. In another example, the refection optic system may be omitted, and the laser light L emitted from the laser light source 120 may be irradiated directly onto the substrate 10.

Additionally, the laser processing machine 100 may further include a stage driving portion which moves the stage 110 along the X, Y, Z axes, and a laser light source controller which regulates an output, a pulse width, and the like of the laser light L.

As illustrated in FIGS. 2 and 3, the laser light L may be relatively moved along a cutting line S (along the X axis in the direction of the arrow in FIG. 3) while locating the focal position P within the substrate 10. For example, as illustrated in FIGS. 2 and 3, the laser light L may be moved along the cutting line S, while the light L is converged at a predetermined depth within the substrate 10 at the focal position P within the substrate 10. Thus, as illustrated in FIG. 4, a laser-scribed layer M, i.e., the modified region M, may be formed within the substrate 10 at the predetermined depth. The laser-scribed layer M formed along the cutting line S, i.e., along a scribe lane, may be a cutting start region.

The converging point P, i.e., the focal position, may be a local position at which the laser light L is converged. In case that the substrate 10 is a silicon wafer, a plurality of die regions may be arranged in a matrix shape and may be divided by the scribe lane. The laser-scribed layer M may be formed either continuously or intermittently within the substrate at the predetermined depth.

For example, when the laser light L is converged within the substrate 10, the laser light L may be absorbed in the vicinity of the converging point P to be melted, expanded, contracted, and solidified, e.g., to have material of the substrate 10 in the vicinity of the converging point P melted, expanded, contracted, and solidified. For example, in the contraction stage of the material, both side regions of the converging point P may be contracted earlier so that a crack may begin to appear in the middle region of the converging point P, followed by growth of the crack in upward and downward directions to form a vertical crack within the substrate 10 after the contraction stage. The laser light L may be irradiated intermittently while moving the laser light L along the cutting line S relatively to the substrate 10, to from the stealth dicing line within the substrate 10 along the X axis, i.e., the modified region M extending into the page in FIG. 4.

The laser-scribed layer M, i.e., the modified region M, may encompass regions with physical characteristics, e.g., density, refractive index, and mechanical strength, different from those of their surroundings. For example, the laser-scribed layer M may have a lattice structure different from a single crystal lattice of a silicon wafer, e.g., the laser-scribed layer M may have a lattice structure different from the crystal lattice of regions of the substrate 10 other than the laser-scribed layer M. Thus, as will be described in more detail below, when an X-ray passes through the laser-scribed region M having a lattice structure with different physical characteristics, e.g., with a broken single crystal lattice, an additional diffraction may occur.

Referring to FIGS. 2 and 4, in example embodiments, when, e.g., before, the laser-scribed layer M is formed within the substrate 10 by the laser processing machine 100, a protection tape 20 may be adhered onto a first surface 12 of the substrate 10. The first surface 12 of the substrate 10 may be an active surface in which circuit elements are formed. The protection tape 20 may protect the circuit elements formed on the first surface 12 of the substrate 10 during a subsequent process. For example, referring to FIGS. 1 and 2, the substrate 10 may be arranged on the stage 110, such that the protection tape 20 faces the stage 110, and the laser light L is irradiated onto a second surface 14 of the substrate 10 that is opposite the first surface 12.

Referring to FIGS. 5 and 6, in example embodiments, the X-ray topographic apparatus 200 may be used to determine whether the laser-scribed layer M has been formed in the substrate 10 by the laser processing machine 100. For example, the substrate 10 may be transferred from the laser processing machine 100 to the X-ray topographic apparatus 200. In another example, the laser irradiation by the laser processing machine 100 and the X-ray irradiation by the X-ray topographic apparatus 200 may be performed in-situ while the substrate 10 is maintained stationary.

As illustrated in FIGS. 5 and 6, the X-ray topographic apparatus 200 may include a stage 210 to support the substrate 10 having the laser-scribed layer M formed by the laser processing machine 100 therein and movable in at least one direction, an X-ray irradiator to irradiate an X-ray into the substrate 10, and an X-ray detector to obtain an image of a diffracted X-ray from the substrate 10. For example, the stage 210 may the same as the stage 110 described previously, e.g., the stage 210 may be formed of a material that transmits X-rays.

In detail, the X-ray irradiator may include a first irradiator 220 which irradiates the X-ray onto the second surface 14 of the substrate 10, and the X-ray detector may include a first detector 230, e.g., a graphic processing unit (GPU) based high-speed image processor to realize a three-dimensional image, which obtains a transmission X-ray topographic image from the first surface 12 of the substrate 10 opposite to the second surface 14.

The first irradiator 220 may irradiate an X-ray at a predetermined incident angle θ with respect to the second surface 14 of the substrate 10 in a predetermined detection region within the cutting line S, and the first detector 230 may detect a diffracted X-ray from the first surface 12 of the substrate 10.

While moving the stage 210 along X axis or Y axis, the X-ray may be moved relatively along the cutting line S. Once the X-ray is irradiated and the X-ray detector obtains the transmission X-ray topographic image, the X-ray topographic image may be analyzed, e.g., a size and a position of the laser-scribed layer M may be measured from the X-ray diffraction image, to determine whether or not the laser-scribed layer M was actually formed in the substrate 10. For example, the size and position of the modified lattice of the laser-scribed layer M may be measured relatively to non-modified regions within the substrate 10, e.g., relative to a non-broken single crystalline lattice, to determine whether the laser-scribed layer M was formed in the substrate 10. For example, analysis of the X-ray diffraction image may be performed in real time, e.g., immediately after obtaining the transmission X-ray topographic image. In other words, analysis of the X-ray diffraction image may be performed before removing the substrate 10 from the X-ray topographic apparatus 200 and/or before grinding or dicing of the substrate 10, so presence or absence of the laser-scribed layer M may be detected before grinding or dicing in order to improve quality and efficiency.

In detail, in example embodiments, the first irradiator 220 may be configured to change the incident angle θ of the X-ray at the same detection region (incident position). For example, the first irradiator 220 may be installed to be rotatable about a central axis parallel with the X axis with respect to the incident position, e.g., the first irradiator 220 may move along the arrows in FIG. 5 around an axis extending into the page). Similarly, the first detector 230 may be installed to be rotatable about a central axis parallel with the X axis with respect to the surface of the substrate 10. The first detector 230 may obtain a 3-dimensional (3D) image of the laser-scribed layer M within the substrate 10 from a plurality of X-ray images at different incident angles.

Figure 7:
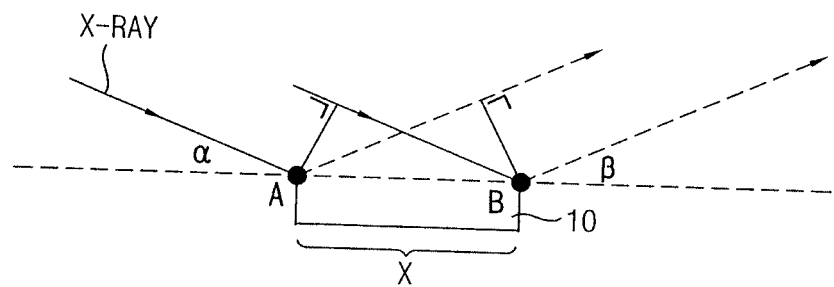
FIG. 7 illustrates a view of a diffraction phenomenon occurring when an X-ray is irradiated onto a crystal lattice of the wafer in FIG. 6.
Figure 8:
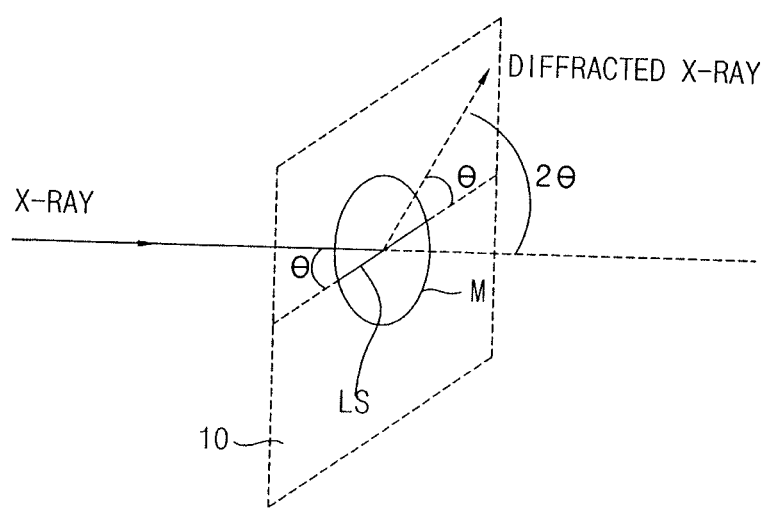
FIG. 8 illustrates a view of a diffraction phenomenon occurring when an X-ray is irradiated onto a lattice surface at the Bragg angle in the wafer of FIG. 7.

Hereinafter, detection of the laser-scribed layer M from a diffracted X-ray image will be explained with reference to FIGS. 7 and 8. FIG. 7 is a view illustrating a diffraction phenomenon occurring when an X-ray is irradiated onto a crystal lattice of the substrate 10 in FIG. 6, and FIG. 8 is a view illustrating a diffraction phenomenon occurring when an X-ray is irradiated onto a lattice surface at the Bragg angle in the substrate 10 of FIG. 7.

Referring to FIG. 7, when an X-ray is irradiated onto a crystal lattice in a wafer, e.g., in the substrate 10, diffracted X-rays from each atom in the crystal may be scattered (dashed arrows in FIG. 7). If the X-ray is monochromatic, the scattered X-rays may interfere with each other, producing diffracted X-rays having a strong pattern in a specific direction. When an X-ray is incident at an angle α and then scattered at an angle β, a light path difference Δ between two points A, B spaced apart by distance x along the surface of the substrate 10 may be represented by the following equation (1).

$$\Delta = x(\cos \alpha - \cos \beta) \quad \text{Equation (1)}$$

When the light path difference Δ is equal to any integer value of the wavelength, nλ, the pattern becomes very strong (constructive interference). When the scattered X-rays on the surface of the substrate 10 are at the same phase (nλ=0), it is obtained that α=β. That is, when an incident angle is equal to a scattering angle, an interference phenomenon with the strongest intensities in the surface of the crystalline lattice is obtained.

Referring to FIG. 8, when monochromatic X-rays are irradiated onto the substrate 10 (the solid line of the laser-scribed layer M is within the dashed substrate 10), an incident X-ray may be incident at an angle (Bragg angle) with respect to a lattice surface LS which satisfies Bragg condition, and hence diffraction may occur. In this case, a direction of the diffraction X-ray (dashed arrow in FIG. 8) may be inclined at an angle θ with respect to the lattice surface LS, and may be inclined at an angle 2θ with respect to the incident X-ray.

When the laser light L is irradiated onto the substrate 10. e.g., onto a single crystalline silicon substrate, to form the laser-scribed layer M, the resultant laser-scribed layer M may have a lattice structure different from the single crystal lattice due to the destruction, e.g., modification, of the single crystal lattice. Because the direction of the lattice in the crystal boundary is formed randomly, the laser-scribed layer M may have the lattice surface LS which satisfied the diffraction condition.

Accordingly, when a X-ray is irradiated onto the substrate 10, a diffracted X-ray from the crystal destruction interface (lattice surface) of the laser-scribed layer M may be detected, e.g., due to different reflection and diffraction angles. Images may be obtained by scanning at regular intervals in the X or Y axis or at different incident angles at a same detection region, and may be synthesized 3-dimensionally into an interior crystal structure. The resultant 3D images may be analyzed to determine presence/absence of the laser-scribed layer M.

As described above, the laser processing machine 100 may irradiate the laser light L into the substrate 10 along the cutting line direction while locating the focal position P within the substrate 10 to form the laser-scribed layer M within the substrate 10. Next, the X-ray topographic apparatus 200 may irradiate an X-ray along the cutting line direction onto the second surface 14 of the substrate 10 (the substrate without the protection tape 20) and obtain an image of a diffracted X-ray from the first surface 12 to determine whether or not the laser-scribed layer M is formed, from the X-ray diffraction image.

Accordingly, before dicing the substrate 10 into individual chips, efficiency and quality of the laser processing may be determined based on the presence of the laser-scribed layer M in-situ in the laser processing process, e.g., a Grinding After Laser (GAL) process. In case that a failure in the laser processing is detected, a subsequent dicing process may be discontinued, to thereby improve efficiency of the dicing process. Further, the measured X-ray diffraction image data may be used for GAL equipment control and variation control between equipment, to thereby improve process efficiency.

Figure 9:
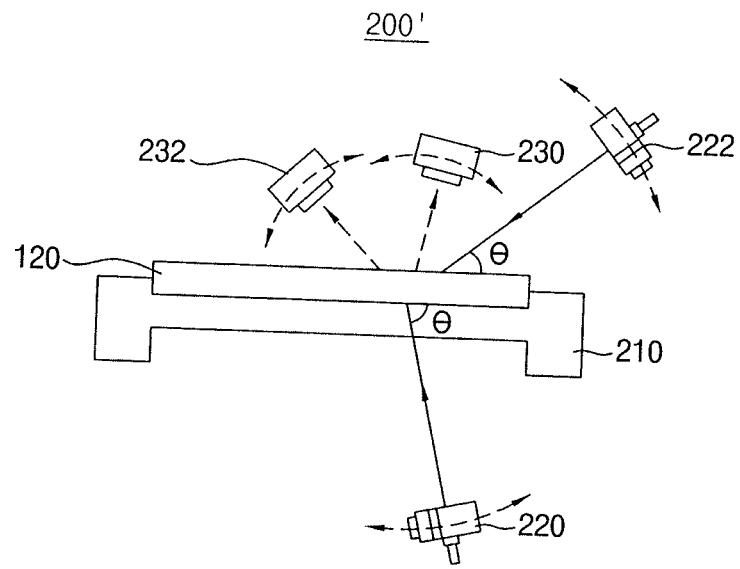
FIG. 9 illustrates a cross-sectional view of an X-ray topographic apparatus of a substrate processing system in accordance with example embodiments.

FIG. 9 is a cross-sectional view illustrating an X-ray topographic apparatus of a substrate processing system in accordance with example embodiments. The X-ray topographic apparatus of a substrate processing system may be substantially the same as or similar to the X-ray topographic apparatus as described with reference to FIG. 5, except for additional elements for obtaining reflection X-ray topographic image. Thus, same reference numerals will be used to refer to the same or like elements and any repetitive explanation concerning the above elements will be omitted.

Referring to FIG. 9, an X-ray topographic apparatus 200' may obtain a transmission X-ray topographic image and a reflection X-ray topographic image from the substrate 10.

In example embodiments, an X-ray irradiator of the X-ray topographic apparatus 200' may include the first irradiator 220 which irradiates an X-ray onto the second surface of the substrate 10 and a second irradiator 222 which irradiates an X-ray onto the first surface of the substrate 10 opposite to the second surface. An X-ray detector of the X-ray topographic apparatus 200 may include the first detector 230 which obtains a transmission X-ray topographic image from the first surface of the substrate 10 and a second detector 232 which obtains a reflection X-ray topographic image from the first surface of the substrate 10.

The first irradiator 220 may irradiate the X-ray at a predetermined incident angle θ with respect to the second surface of the substrate 10 within the cutting line S. and the first detector 230 may detect a diffracted X-ray from the first surface of the substrate 10. The second irradiator 222 may irradiate the X-ray at a predetermined incident angle θ with respect to the first surface of the substrate 10 in the same detection position within the cutting line S. and the second detector 232 may detect a diffracted X-ray from the first surface of the substrate 10.

For example, while moving the stage 210 along the X axis or the Y axis, the X-ray may be moved relatively to the stage 210 along the cutting line S. In another example, the X-ray may be moved along the X axis or the Y axis along the cutting line S relative to stage 210, e.g., while the stage 210 remains stationary.

Accordingly, a size and position of the laser-scribed layer M may be detected more precisely from the transmission X-ray diffraction image and the reflection X-ray diffraction image.

In example embodiments, the second irradiator 222 may be configured to change the incident angle θ of the X-ray at the same detection region (incident position). For example, the second irradiator 222 may be installed to be rotatable about a central axis parallel with X axis with respect to the incident position. Similarly, the second detector 232 may be installed to be rotatable about a central axis parallel with X axis with respect to the surface of the substrate 10. The first detector 230 may obtain a 3D image of the laser-scribed layer M within the substrate 10 from a plurality of X-ray images at different incident angles.

Figure 10:
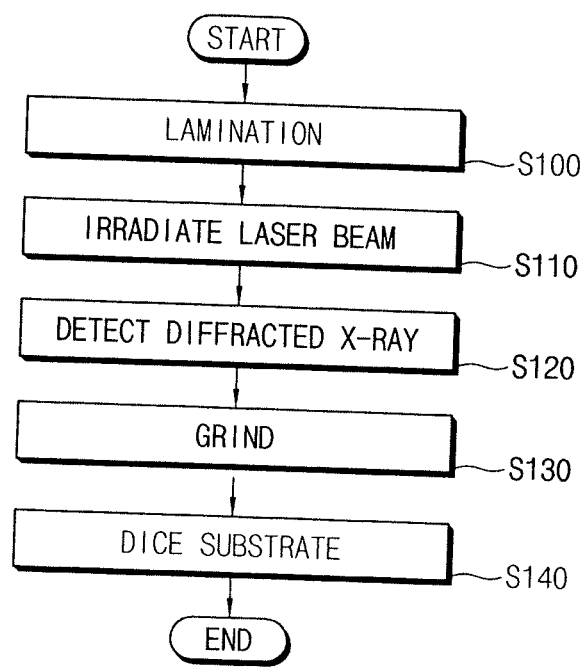
FIG. 10 illustrates a flow chart of a substrate dicing method in accordance with example embodiments.

Hereinafter, a method of dicing the substrate 10 using the substrate processing system will be explained with reference to FIGS. 10 and 11A-11E. FIG. 10 is a flow chart illustrating a substrate dicing method in accordance with example embodiments, and FIGS. 11A to 11E are views illustrating stages in the substrate dicing method in accordance with example embodiments.

Figure 11A:
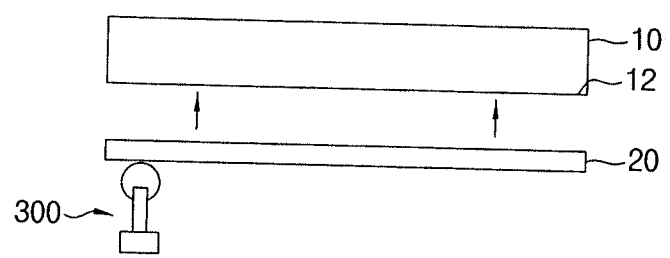
FIGS. 11A to 11E illustrate views of stages in a substrate dicing method in accordance with example embodiments.

First, referring to FIGS. 10 and 11A, the protection tape 20 for protecting circuit elements may be adhered onto the first surface 12 (active surface) of the substrate 10, i.e., operation S100. The protection tape 20 may be adhered by a tape adhering apparatus 300, e.g., lamination.

Figure 11B:
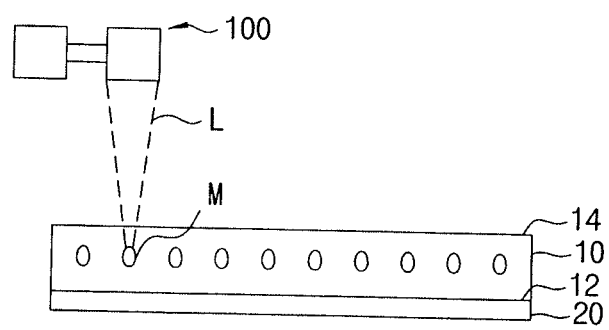

Next, referring to FIGS. 10 and 11B, the laser processing machine 100 may irradiate the laser light L onto the second surface 14 of the substrate 10 opposite to the first surface 12, i.e., operation S110. The laser light L may be moved, e.g., scanned, along the cutting line S (FIG. 3) to form the laser-scribed layer M within the substrate 10, e.g., at a predetermined depth within the substrate 10, along the cutting line S. For example, as illustrated in FIG. 11B, the laser light L may form multiple laser-scribed layer M spaced from each other within the substrate 10.

In example embodiments, the protection tape 20 may be adhered onto the first surface 12 of the substrate 10 using the tape adhering apparatus 300. The protection tape 20 may protect the circuit elements formed in the first surface 12 of the substrate 10.

Then, the laser light L may be irradiated into the substrate 10, while locating the converging point P within the substrate 10, to form an optically damaged portion, i.e., the laser-scribed layer M, within the substrate 10 by multiphoton absorption. The laser light L may be moved relatively along the cutting line S to form the laser-scribed layer M as the modified region within the substrate 10. The laser-scribed layer M formed along the cutting line S, i.e., a scribe lane, may be a cutting start region.

The laser-scribed layer M as the modified region may have a lattice structure different from a single crystal lattice of a silicon wafer. Thus, as described below, when an X-ray passes through laser-scribed layer M with the different lattice structure, i.e., having a modified single crystal lattice, an additional diffraction occurs.

Figure 11C:
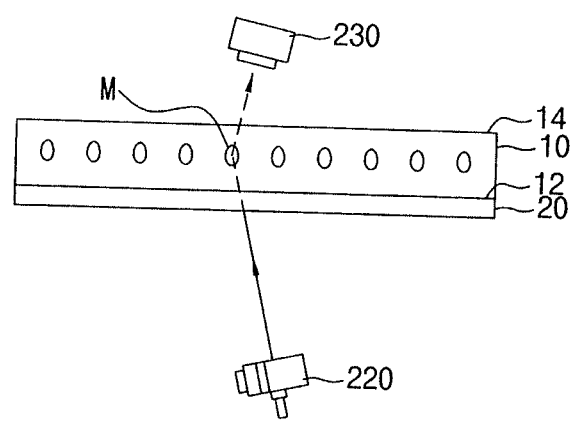

Then, referring to FIGS. 10 and 11C, a diffracted X-ray may be detected from the substrate 10 to determine whether or not the laser-scribed layer M is formed, i.e., operation S120. In example embodiments, the first X-ray irradiator 220 of the X-ray topographic apparatus may irradiate an X-ray at a predetermined incident angle θ with respect to the first surface of the substrate 10 in a predetermined detection region within the cutting line S, and the first X-ray detector 230 may detect the diffracted X-ray from the second surface of the substrate 10.

While moving the stage 210 along the X axis or the Y axis, the X-ray may be moved relatively along the cutting line S. A size and position of the laser-scribed layer M may be measured from the X-ray diffraction image.

The first X-ray irradiator 220 may be configured to change the incident angle θ of the X-ray at the same detection region (incident position). For example, the first X-ray irradiator 220 may be installed to be rotatable about a central axis parallel with X axis with respect to the incident position. Similarly, the first X-ray detector 230 may be installed to be rotatable about a central axis parallel with X axis with respect to the surface of the substrate 10. The first X-ray detector 230 may obtain a 3D image of the laser-scribed layer M within the substrate 10 from a plurality of X-ray images at different incident angles. Further, as described previously, a second X-ray irradiator may irradiate an X-ray at a predetermined incident angle θ with respect to the second surface of the substrate 10 within the cutting line 5, and a second X-ray detector may detect a diffracted X-ray from the second surface of the substrate 10.

Accordingly, a size and position of the laser-scribed layer M may be detected more precisely from the transmission X-ray diffraction image and the reflection X-ray diffraction image.

Figure 11D:
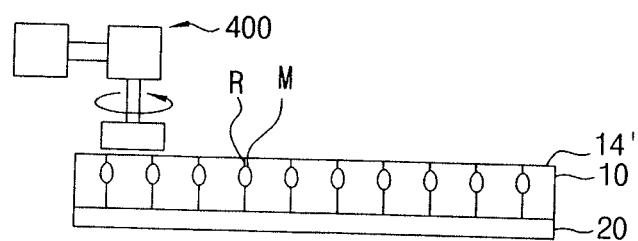

Next, referring to FIGS. 10 and 11D, the second surface 14 of the substrate 10 may be ground (S130). That is, the second surface 14 (backside) of the substrate 10 having the laser-scribed layer M formed therein may be ground using a grinding apparatus 400.

The second surface 14 of the substrate 10 may be thinned. That is, the substrate 10 may be, e.g., uniformly, ground from the direction of the second surface 14 to reduce a total thickness of the substrate 10, e.g., to have a predetermined thickness. For example, as illustrated in FIG. 11D, the laser-scribed layer M may function as a dicing start region to form a vertical crack R therefrom, e.g., the substrate 10 may be ground from the direction of the second surface 14 until a new second surface 14' is only slightly above the laser-scribed layer M with the vertical cracks R extending from the first surface 12 to the new second surface 14' through the laser-scribed layers M.

Figure 11E:
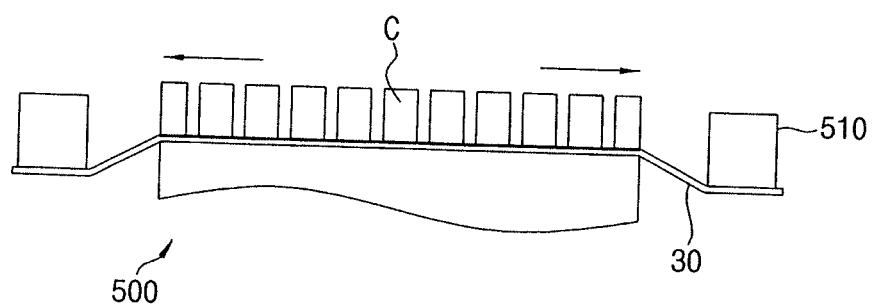

Then, referring to FIGS. 10 and 11E, the substrate 10 may be diced into individual chips C, i.e., operation S140. The dicing may be performed by separating the substrate 10 into the individual chips C through the vertical cracks R.

Next, in example embodiments, an adhesive tape sheet 30 may be adhered onto the second surface (backside) of the substrate 10 using a mask ring 510 of an annular shape, and then, the adhesive tape sheet 30 may be expanded using a tape expander 500 to divide the substrate 10 into individual chips C along the cutting line S. For example, the individual chips C on the adhesive tape sheet 30 may be spaced apart from each other in a radial direction. Then, the individual chips C may be packaged respectively to form semiconductor packages.

The above-mentioned processes may be reiterated to manufacture a semiconductor package including a logic device or a memory device. For example, the semiconductor package may include logic devices, e.g., central processing units (CPUs), main processing units (MPUs), or application processors (APs), or the like, and volatile memory devices, e.g., dynamic random-access memory (DRAM) devices, static random-access memory (SRAM) devices, or non-volatile memory devices, e.g., flash memory devices, phase-change random-access memory (PRAM) devices, magnetoresistive random-access memory (MRAM) devices, resistive random-access memory (ReRAM) devices, or the like.

By way of summation and review, there has not been a way to inspect a modified region of a wafer or substrate irradiated by a laser light, e.g., a chip, before completion of a dicing process. Further, a visual inspection may be performed only on a cross section of the diced chip, after completion of the dicing. Therefore, product quality and yield rates of a laser machining process may be deteriorated.

In contrast, example embodiments provide a laser processing method capable of monitoring in real time a modified region formed by a laser light. Example embodiments also provide a method of dicing a substrate using the above laser processing method. Example embodiments also provide a substrate processing system, e.g., a substrate processing apparatus, for performing the above laser processing method.

That is, according to example embodiments, a laser light may be irradiated into a substrate along a cutting line to form a laser-scribed layer, and then, an X-ray may be irradiated along the cutting line onto a first surface of the substrate to obtain an image of a diffracted X-ray from a second surface of the substrate. Whether or not the laser-scribed layer was formed may be determined from the X-ray diffraction image.

Accordingly, before dicing the substrate into individual chips, efficiency and quality of the laser processing may be determined based on the presence of the laser-scribed layer in-situ in the laser processing process. In case that a failure is detected in the laser processing, without proceeding to a subsequent dicing process, the laser processing process may be corrected, to thereby improve efficiency of the dicing process. Further, the measured X-ray diffraction image data may be used for a laser processing equipment control and variation control between equipment, to thereby improve process efficiency.

The methods and processes described herein may be performed by code or instructions to be executed by a computer, processor, manager, or controller. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A laser processing method, the method comprising:
irradiating a laser light into a substrate along a cutting line to form a laser-scribed layer within the substrate;
irradiating an X-ray onto a first surface of the substrate along the cutting line;
obtaining an image of a diffracted X-ray from the substrate; and
determining whether or not the laser-scribed layer is formed along the cutting line, based on analysis of the obtained image of the diffracted X-ray.

2. The laser processing method as claimed in claim 1, wherein forming the laser-scribed layer includes moving at least one of the laser light and the substrate relatively to each other along the cutting line.

3. The laser processing method as claimed in claim 1, wherein obtaining the image of the diffracted X-ray from the substrate includes obtaining a transmission X-ray topographic image from a second surface of the substrate opposite to the first surface.

4. The laser processing method as claimed in claim 3, wherein obtaining the image of the diffracted X-ray from the substrate further includes obtaining a reflection X-ray topographic image from the first surface of the substrate.

5. The laser processing method as claimed in claim 1, wherein obtaining the image of the diffracted X-ray from the substrate includes obtaining a reflection X-ray topographic image from the first surface of the substrate.

6. The laser processing method as claimed in claim 1, wherein irradiating the X-ray onto the first surface of the substrate includes irradiating the X-ray while changing an incident angle of the X-ray at a same detection region.

7. The laser processing method as claimed in claim 6, wherein obtaining the image of the diffracted X-ray from the substrate includes obtaining a 3-dimensional image of the laser-scribed layer from a plurality of X-ray images at different incident angles.

8. The laser processing method as claimed in claim 1, wherein determining whether or not the laser-scribed layer is formed includes measuring a size and a position of the laser-scribed layer from the obtained image of the diffracted X-ray.

9. The laser processing method as claimed in claim 1, wherein irradiating the X-ray includes moving at least one of the X-ray and the substrate relatively to each other along the cutting line.

10. The laser processing method as claimed in claim 1, further comprising grinding the first surface of the substrate.

11. A substrate dicing method, the method comprising:
irradiating a laser light into a substrate along a cutting line to form a laser-scribed layer within the substrate;
irradiating an X-ray onto a first surface of the substrate along the cutting line;
obtaining an image of a diffracted X-ray from the substrate;
determining whether or not the laser-scribed layer is formed along the cutting line, based on analysis of the obtained image of the diffracted X-ray; and
grinding the first surface of the substrate.

12. The substrate dicing method as claimed in claim 11, further comprising forming a protection tape on a second surface of the substrate opposite to the first surface, before irradiating the laser light.

13. The substrate dicing method as claimed in claim 11, wherein forming the laser-scribed layer includes moving at least one of the laser light and the substrate relatively to each other along the cutting line.

14. The substrate dicing method as claimed in claim 13, wherein obtaining the image of the diffracted X-ray from the substrate includes obtaining a transmission X-ray topographic image from a second surface of the substrate opposite to the first surface.

15. The substrate dicing method of claim 14, wherein obtaining the image of the diffracted X-ray from the substrate further includes obtaining a reflection X-ray topographic image from the first surface of the substrate.

16. The substrate dicing method as claimed in claim 11, wherein irradiating the X-ray onto the first surface of the substrate includes irradiating the X-ray while changing an incident angle of the X-ray at a same detection region.

17. The substrate dicing method as claimed in claim 11, wherein obtaining the image of the diffracted X-ray from the substrate includes obtaining a 3-dimensional image of the laser-scribed layer from a plurality of X-ray images at different incident angles.

18. The substrate dicing method as claimed in claim 11, wherein irradiating the X-ray includes moving at least one of the X-ray and the substrate relatively to each other along the cutting line.

19. The substrate dicing method as claimed in claim 11, wherein determining whether or not the laser-scribed layer is formed includes measuring a size and a position of the laser-scribed layer from the obtained image of the diffracted X-ray.

20. The substrate dicing method as claimed in claim 11, further comprising:
adhering an adhesive tape sheet onto the first surface of the substrate; and
expanding the adhesive tape sheet along the cutting line to dice the substrate into individual chips.

* * * * *